United States Patent [19]

Löher et al.

[11] Patent Number: 5,030,270
[45] Date of Patent: Jul. 9, 1991

[54] SULFONYLUREAS WITH HETEROCYCLIC SUBSTITUENTS, AND THE USE THEREOF AS HERBICIDES OR PLANT-GROWTH REGULATORS

[75] Inventors: Heinz-Josef Löher, Hofheim am Taunus; Lothar Willms, Hillscheid; Michael Frey, Neusäss; Klaus Bauer, Hanau; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 389,070

[22] Filed: Aug. 3, 1989

[30] Foreign Application Priority Data

Aug. 5, 1988 [DE] Fed. Rep. of Germany ....... 3826609

[51] Int. Cl.$^5$ .................. A01N 43/54; C07D 239/47; C07D 239/48; C07D 239/42
[52] U.S. Cl. ........................................ 71/92; 544/319; 544/320; 544/321; 544/323; 544/324; 544/327; 544/331; 544/332; 544/333; 544/335
[58] Field of Search .................... 71/92; 544/319, 320, 544/321, 323, 324, 327, 331, 332, 333, 334, 334

[56] References Cited

U.S. PATENT DOCUMENTS

| | | | |
|---|---|---|---|
| 4,440,565 | 4/1984 | Willms et al. | 71/93 |
| 4,492,598 | 1/1985 | Willms et al. | 71/93 |
| 4,601,747 | 7/1986 | Willms et al. | 71/92 |

FOREIGN PATENT DOCUMENTS

| | | |
|---|---|---|
| 11811/83 | 9/1983 | Australia . |
| 2110689 | 6/1983 | United Kingdom . |

*Primary Examiner*—John M. Ford
*Attorney, Agent, or Firm*—Curtis, Morris & Safford

[57] ABSTRACT

Sulfonylureas with heterocyclic substituents, a process for the preparation thereof, and the use thereof as herbicides or plant-growth regulators.

Sulfonylureas with heterocyclic substituents, of the formula

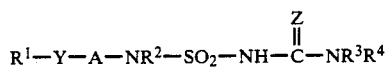

in which the variables are defined in the specification, as well as the salts thereof have herbicidal and plant-growth regulatory properties on mon- and dicotyledonous plants.

14 Claims, No Drawings

SULFONYLUREAS WITH HETEROCYCLIC SUBSTITUENTS, AND THE USE THEREOF AS HERBICIDES OR PLANT-GROWTH REGULATORS

It has been disclosed that alkylsulfonylureas with heterocyclic substituents have herbicidal and plant-growth regulating properties (see EP-A 061,661, EP-A 071,958, EP-A 131,258, German Offenlegungsschrift 3,243,533). However, some of these have disadvantages when used, such as, for example, a high persistence or inadequate selectivity in important useful crops.

New heterocyclic sulfonylureas with advantageous herbicidal properties have now been found.

The present invention relates to compounds of the general formula (I)

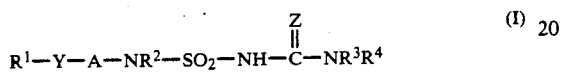

in which

A denotes a saturated or unsaturated, unbranched or branched $C_1$–$C_{10}$-hydrocarbon radical, preferably a radical of the formula $CH_2$, $CH_2CH_2$, $CHR$, $CRR'$, $CH_2CHR$ or $CH_2CRR'$, where R and R', denote, independently of one another, $C_1$–$C_4$-alkyl or $C_2$–$C_4$-alkenyl, $R^1$ denotes $C_1$–$C_8$-alkyl, $C_2$–$C_8$-alkenyl, $C_2$–$C_8$-alkynyl, $C_3$–$C_8$-cycloalkyl, $C_5$–$C_8$-cycloalkenyl or one of the preceding five radicals which is substituted one or more times by halogen or by the radicals selected from the group comprising $C_1$–$C_6$-alkoxy, $C_2$–$C_6$-alkenyloxy, $C_2$–$C_6$-alkynyloxy, $C_1$–$C_6$-alkylthio, $C_1$–$C_6$-alkylsulfinyl, $C_1$–$C_6$-alkylsulfonyl, $C_3$–$C_6$-cycloalkyl, a radical of a three- to six-membered saturated heterocycle having one oxygen atom in the ring, furyl, phenyl and a phenyl radical which is substituted one or more times by radicals from the group comprising halogen, $C_1$–$C_4$-alkyl, $C_1$–$C_4$-alkoxy, $CF_3$, ($C_1$–$C_4$-alkoxy)-carbonyl and nitro, or $R^1$ denotes phenyl or a phenyl radical which is substituted one or more times by radicals from the group comprising halogen, $C_1$–$C_4$-alkyl, $C_1$–$C_4$-alkoxy, $CF_3$, ($C_1$–$C_4$-alkoxy)-carbonyl and nitro, or $R^1$ denotes a radical of the formula —CO—$R^5$, —CHR$^6$—COOR$^7$, —CHR$^6$—CH$_2$—COOR$^7$ or CH$_2$—CHR$^6$—COOR$^7$, where, in the formulae, $R^5$ represents $C_1$–$C_6$-alkyl, $R^6$ represents hydrogen, $C_1$–$C_4$-alkyl, phenyl or benzyl and $R^7$ represents $C_1$–$C_4$-alkyl, phenyl or benzyl, Y denotes S or $SO_2$, $R^2$ denotes H, $C_1$–$C_8$-alkyl, $C_2$–$C_8$-alkenyl, $C_2$–$C_8$-alkynyl or one of the preceding three radicals which is substituted one or more times by halogen or by radicals from the group comprising $C_1$–$C_6$-alkoxy, $C_2$–$C_6$-alkenyloxy, $C_2$–$C_6$-alkynyloxy, $C_1$–$C_6$-alkylthio, $C_1$–$C_6$-alkylsulfinyl, $C_1$–$C_6$-alkylsulfonyl, ($C_1$–$C_6$-alkoxy)-carbonyl, phenoxycarbonyl, benzyloxycarbonyl and phenyl, denotes $C_3$–$C_8$-cycloalkyl which is unsubstituted or substituted one or more times by halogen or once or twice by $C_1$–$C_4$-alkoxy or $C_1$–$C_4$-$C_4$-alkylthio, denotes $C_5$–$C_8$-cycloalkenyl, cyclopropylmethyl, epoxypropyl, furfuryl, tetrahydrofurfuryl, phenoxy-$_1$–$C_6$-alkyl, phenyl or one of the last two preceding radicals which is substituted in the phenyl ring by halogen, $C_1$–$C_4$-alkyl, $C_1$–$C_4$-alkoxy or nitro, $R^3$ denotes H, $C_1$–$C_8$-alkyl, $C_2$–$C_8$-alkenyl, $C_2$–$C_8$-alkynyl or $C_1$–$C_4$-alkoxy, $R^4$ denotes a radical of the formula

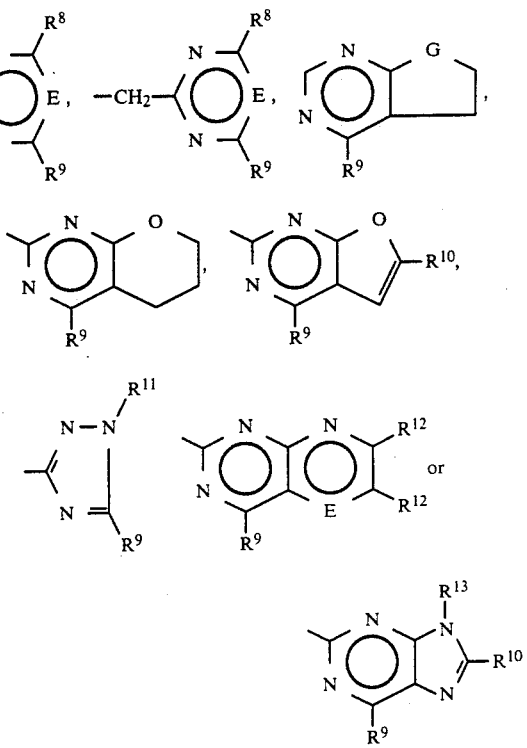

$R^8$ and $R^9$ denote, independently of one another, H, halogen, $C_1$–$C_6$-alkyl, $C_1$–$C_6$-alkoxy, $C_1$–$C_6$-alkylthio or one of the last three preceding radicals which is substituted one or more times by halogen or once or twice by $C_1$–$C_4$-alkoxy or $C_1$–$C_4$-alkylthio, or denote a radical $NR^{14}R^{15}$, $C_3$–$C_6$-cycloalkyl, —OCHR$^{1-6}$COOR$^{17}$, $C_3$–$C_5$-alkenyl, $C_2$–$C_4$-alkynyl, $C_3$–$C_5$-alkenyloxy or $C_3$–$C_5$-alkynyloxy, $R^{10}$ denotes hydrogen or $C_1$–$C_4$-alkyl, $R^{11}$ denotes $C_1$–$C_4$-alkyl, —CHF$_2$ or —CH$_2$CF$_3$, $R^{12}$ denote, independently of one another, H, $C_1$–$C_4$-alkyl, $C_1$–$C_4$-alkoxy or halogen, $R^{13}$ denotes hydrogen, $C_1$–$C_4$-alkyl, CHF$_2$ or CH$_2$CF$_3$, $R^{14}$ and $R^{15}$ denote, independently of one another, H, $C_1$–$C_4$-alkyl, $C_2$–$C_4$-alkenyl or $C_3$–$C_4$-alkynyl, $R^{16}$ denotes hydrogen or $C_1$–$C_4$-alkyl, $R^{17}$ denotes hydrogen or $C_1$–$C_4$-alkyl, E denotes CH or N, G denotes CH$_2$ or O and Z denotes O or S, as well as the salts thereof.

The compounds of the formula (I) can form salts in which the hydrogen of the —$SO_2$—NH-group is replaced by a cation suitable for agriculture. Examples of these salts are metal salts, especially alkali metal and alkaline earth metal salts, as well as optionally alkylated ammonium or organic amine salts. They are preferably prepared in solvents inert under the reaction conditions, such as water, methanol or acetone, at temperatures from 0° to 100° C., from the compounds of the formula (I). Examples of suitable bases for preparing the salts according to the invention are alkali metal carbonates, such as potassium carbonate, as well as alkali metal and alkaline earth metal hydroxides, as well as ammonia and ethanolamine.

Of particular interest are compounds of the formula (I) according to the invention in which $R^1$ denotes $C_1-C_4$-alkyl, a $C_1-C_4$-alkyl radical which is substituted one or more times by halogen or once or twice by $C_1-C_4$-alkoxy, $C_2-C_3$-alkenyloxy, $C_2-C_3$-alkynyloxy, $C_1-C_4$-alkylthio, $C_1-C_4$-alkylsulfinyl, $C_1-C_4$-alkylsulfonyl, phenyl or a phenyl radical which is substituted one to three times by radicals from the group comprising halogen, $C_1-C_4$-alkyl, $C_1-C_4$-alkoxy, $CF_3$, $(C_1-C_4$-alkoxy)-carbonyl and nitro, or denotes $C_3-C_8$-cycloalkyl or a $C_3-C_8$-cycloalkyl radical which is substituted one or more times by halogen or once or twice by $C_1-C_4$-alkoxy or $C_1-C_4$-alkylthio, or denotes $C_5-C_8$-cycloalkenyl, cyclopropylmethyl, epoxypropyl, furfuryl, tetrahydrofurfuryl, benzyl, phenyl or a benzyl or phenyl radical which is substituted in the phenyl ring by one or more radicals from the group comprising halogen, $C_1-C_4$-alkyl, $C_1-C_4$-alkoxy, $CF_3$, $(C_1-X_4$-alkoxy)-carbonyl and nitro, or denotes a radical of the formula —$COR^5$, $CHR^6$—$COOR^7$, $CHR^6$—$CH_2$—$COOR^7$ or $CH_2$—$CHR^6$—$COOR^7$, $R^5$ denotes $C_1-C_4$-alkyl,
$R^6$ denotes H, $C_1-C_4$-alkyl, benzyl or phenyl and
$R^7$ denotes H, $C_1-C_4$-alkyl, benzyl or phenyl.

Of particular interest are compounds of the formula (I) according to the invention in which
$R^2$ denotes $C_1-C_4$-alkyl, a $C_1-C_4$-alkyl radical which is substituted one or more times by halogen or once or twice by $C_1-C_4$-alkoxy, $C_2-C_4$-alkenyloxy, propargyloxy, $C_1-C_4$-alkylthio, $C_1-C_4$-alkylsulfinyl, $C_1-C_4$-alkylsulfonyl, $(C_1-C_4$-alkoxy)-carbonyl, phenoxycarbonyl, benzyloxycarbonyl or phenyl, or denotes $C_3-C_8$-cycloalkyl.

Additionally of particular interest are compounds of the formula (I) according to the invention in which $R^4$ denotes a radical of the formula

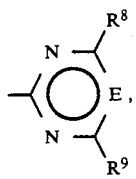

and
$R^8$ and $R^9$ denote, independently of one another, halogen, $C_1-C_4$-alkyl, $C_1-C_4$-alkoxy, $C_1-C_4$-alkylthio or one of the last three preceding radicals which are substituted one or more times by halogen or once or twice by $C_1-C_4$-alkoxy, $C_1-C_4$-alkylthio, or denote a radical $NR^{14}R^{15}$, $C_3-C_6$-cycloalkyl, —$OCHR^{1-6}COOR^{17}$, allyl, propargyl, allyloxy or propargyloxy,
$R^{14}$ and $R^{15}$ denote, independently of one another, H or $C_1-C_4$-alkyl,
$R^{16}$ denotes H or $C_1-C_4$-alkyl,
$R^{17}$ denotes $C_1-C_4$-alkyl and
E denotes CH or N.

Preferred compounds of the formula (I) are those in which
A denotes a radical of the formula —$CH_2$— or —$CH_2$—$CH_2$—,
$R^1$ denotes $C_1-C_4$-alkyl, a $C_1-C_4$-alkyl radical which is substituted one or more times by halogen or once or twice by $C_1-C_4$-alkoxy, denotes $C_3-C_8$-cycloalkyl which is substituted one or more times by halogen or is unsubstituted, denotes benzyl, phenyl or a benzyl or phenyl radical which is substituted in the phenyl ring one or more times by halogen, $C_1-C_4$-alkyl, $C_1-C_4$-alkoxy, $CF_3$, $(C_1-C_4$-alkoxy)-carbonyl or nitro, or denotes a radical of the formula

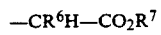
—$CR^6H$—$CO_2R^7$ in which $R^6$ and $R^7$ are identical or different and each denotes H, $C_1-C_4$-alkyl, phenyl or benzyl,
$R^2$ denotes $C_1-C_4$-alkyl which is unsubstituted or substituted one or more times by halogen or by $(C_1-C_4$-alkoxy)-carbonyl, phenyloxycarbonyl, benzyloxycarbonyl or phenyl,
$R^3$ denotes H, $C_1-C_4$-alkyl or allyl, especially H,
$R^4$ denotes a radical of the formula

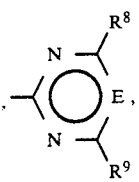

$R^8$ and $R^9$ denote, independently of one another, halogen, $C_1-C_4$-alkyl, $C_1-C_4$-alkoxy or one of the last two preceding radicals which is halogenated, especially the radicals $CH_3$, $OCH_3$, $OC_2H_5$, Cl, $OCF_2H$, $CF_3$,
E denotes CH or N and
Z denotes O or S.

The present invention furthermore relates to the process for the preparation of compounds of the general formula (I) or the salts thereof, which comprises
(a) reacting a compound of the formula (II)

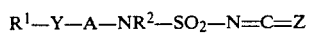
$R^1$—Y—A—$NR^2$—$SO_2$—N=C=Z    (II)

with a compound of the formula (III)

H—$NR^3R^4$    (III)

where in formulae (II) and (III) A, Y, Z, $R^1$, $R^2$, $R^3$ and $R^4$ have the meanings specified for formula (I), or
(b) reacting a compound of the formula (IV)

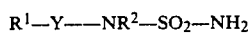
$R^1$—Y—$NR^2$—$SO_2$—$NH_2$    (IV)

with a carbamate or thiocarbamate of the formula (V)

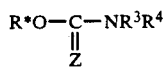

where in the formulae (IV) and (V) $R^1$, $R^2$, $R^3$, $R^4$, A, Y and Z have the meanings specified for formula (I), and R* denotes $C_1-C_6$-alkyl, $C_1-C_4$-halogenoalkyl, phenyl or a phenyl radical which is substituted one or more times by halogen, $C_1-C_4$-alkyl or nitro or
(c) reacting a carbamate or thiocarbamate of the formula (VI) with a compound of the abovementioned formula (III)

$$R^1-Y-A-NR^2-SO_2-NH-\underset{\underset{Z}{\|}}{C}-OR^* \quad (VI)$$

where $R^1$, $R^2$, $R^*$, Y, A and Z have the said meanings, or (d) reacting a compound of the formula (VII) or (VIII)

$$R^1-Y-A-NH-R^2 \quad (VII)$$

$$R^1-Y-A-NH-R^2 \times HCl \quad (VIII)$$

with a compound of the formula (IX)

$$ClSO_2-NH-\underset{\underset{Z}{\|}}{C}-NR^3R^4 \quad (IX)$$

where in the formulae (VII) to (IX) A, Y, Z, $R^1$, $R^2$, $R^3$ and $R^4$ have the meanings specified above.

The reaction of compounds of the formula (II) and (III) is preferably carried out in aprotic solvents which are inert under the reaction conditions, such as, for example, acetonitrile, dichloromethane, toluene, tetrahydrofuran or dioxane at temperatures from 0° C. to the boiling point of the reaction mixture. The alkylsulfonyl isocyanates and isothiocyanates of the formula (II) can be prepared in analogy to customary procedures from the corresponding sulfonamides of the abovementioned formula (IV) in a straightforward manner (cf., for example, EP-A 085,276).

The starting materials of the formula (III) are known or can be prepared by procedures known in principle, for example by cyclization of corresponding guanidine derivatives with appropriately substituted 1,3-diketones; cf., for example, "The chemistry of heterocyclic compounds" Vol. XVI (1962) and supplement I (1970). Another possibility comprises derivatization of cyanuric chloride; cf., for example, "The chemistry of heterocyclic compounds" L. Rapaport: "s-Triazines and Derivatives" (1959).

The reaction of a compound (IV) with a heterocyclic carbamate of the formula (V) is preferably carried out in the presence of tertiary organic bases, for example 1,8-diazabicyclo[5.4.0]undec-7-ene (DBU), in inert solvents such as acetonitrile or dioxane at a temperature of 20° C. up to the boiling point of the reaction mixture; the process is analogous to the corresponding process from EP-A 44,807. The carbamates (V) required for this are known from the literature or are prepared in analogy to processes which are known or customary per se; an appropriate process is described in EP-A 70,804.

The carbamates of the formula (VI) are new and can be prepared by reaction of the compounds of the formula (IV) with appropriate chloroformic esters (cf. EP-A 87,780). The reaction of the carbamates or thiocarbamates of the formula (VI) with the aminoheterocycles of the formula (III) is preferably carried out in inert solvents, for example toluene, xylene, chlorobenzene, dioxane and acetonitrile, at a temperature of 20° C. up to the boiling point of the relevant reaction mixture.

The compounds of the formula (VII) can be prepared from compounds of the formula (VIII) with bases. Compounds of the formulae (VIII) and (IX) can be prepared in analogy to processes which are known from the literature or customary per se (cf. U.S. Pat. No. 4,016,266 and J. Heterocycl. Chem. 8, 597 (1971)).

The sulfonylureas of the formula (I) which contain one or more asymmetric carbon atoms in the aliphatic radicals A, $R^1$ and $R^2$ are in the form of enantiomers and/or diastereomers. In general, the corresponding compounds according to the invention are obtained as racemates or as mixtures of diastereomers. If desired, the customary techniques can be used to separate these mixtures into the sterically homogeneous constituents. It is also possible to prepare the said compounds pure by using sterically homogeneous starting materials.

The formula (I) therefore embraces all the abovementioned enantiomeric and diastereomeric forms of the compounds defined above.

The compounds of the formula I according to the invention display an excellent herbicidal activity against a wide spectrum of economically important mono- and dicotyledonous harmful plants. The active compounds also deal well with perennial weeds which emerge from rhizomes, rootstocks or other persistent organs and are difficult to control. In this connection it is immaterial whether the substances are applied in a presowing, preemergence or post emergence process. Some specific representatives of the mono- and dicotyledonous weed flora which can be controlled by the compounds according to the invention may be mentioned by way of example, without intending a restriction to specific species by the mention.

Those dealt with well are, on the side of monocotyledonous weed species, for example, Avena, Lolium, Alopecurus, Phalaris, Echinochloa, Digitaria, Setaria and Cyperus species from the annual group and on the side of perennial species Agropyron, Cynodon, Imperata as well as Sorghum and perennial Cyperus species too.

For dicotyledonous weed species, the spectrum of action extends to species such as, for example, Galium, Viola, Veronica, Lamium, Stellaria, Amaranthus, Sinapis, Ipomoea, Matricaria, Abutilon and Sida on the annual side as well as Convolvulus, Cirsium, Rumex and Artemisia in the perennial weeds.

Weeds occurring under the specific cultivation conditions in rice, such as, for example Sagittaria, Alisma, Eleocharis, Scirpus and Cyperus, are likewise excellently controlled by the active substances according to the invention.

When the compounds according to the invention are applied to the soil surface before germination, either there is complete prevention of emergence of weed plantlets or the weeds grow to the cotyledonous stage but then cease to grow and finally die off completely after three to four weeks have elapsed.

When the active substances are applied to the green parts of the plants in the post emergence process, once again a drastic cessation of growth occurs very rapidly after the treatment, and the weed plants remain in the growth stage present at the time of application or die off entirely after a certain time, so that competition from weeds which is harmful for the crop plants is eliminated in this way very early and permanently.

Although the compounds according to the invention display an excellent herbicidal activity against mono- and dicotyledonous weeds, the damage to crop plants of economically important crops such as, for example, wheat, barley, rye, rice, corn, sugar beet, cotton and soybean is only inconsiderable or zero. For these reasons, the present compounds are very well suited for the selective control of undesired plant growth in plantations of agricultural use.

Furthermore, the substances according to the invention display excellent growth-regulatory properties in crop plants. They intervene to regulate the plants' own metabolism and can thus be employed to influence specifically plant constituents and to facilitate harvesting, such as, for example, by inducing desiccation and stunting of growth. Furthermore, they are also suitable for general control and inhibition of undesired vegetative growth without at the same time killing the plants. Inhibition of vegetative growth plays a large part in many mono- and dicotyledonous crops because it is possible in this way to reduce or completely prevent lodging.

The compounds according to the invention can be used in the form of wettable powders, emulsifiable concentrates, sprayable solutions, dusting agents or granules in the customary formulations.

Hence the invention also relates to herbicidal and growth-regulating agents which contain a compound of the formula I in combination with customary formulating auxiliaries and inert substances, as well as to the use thereof in the agricultural sector.

Wettable powders are products which can be dispersed homogeneously in water and which contain besides the active substance, and apart from a diluent or inert substance where appropriate, also wetting agents, for example polyethoxylated alkylphenols, polyethoxylated fatty alcohols, alkyl- or alkylphenylsulfonates and dispersing agents, for example sodium ligninsulfonate, sodium 2,2'-dinaphthylmethane-6,6'-disulfonate, sodium dibutylnaphthalenesulfonate or else sodium oleoylmethyltaurate. The preparation is carried out in a customary manner, for example by milling and mixing the components.

Emulsifiable concentrates can be prepared, for example, by dissolving the active substance in an inert organic solvent, for example butanol, cyclohexanone, dimethylformamide, xylene or else higher-boiling aromatic compounds or hydrocarbons with the addition of one or more emulsifiers. In the case of liquid active substances, the solvent content can also be entirely or partially dispensed with. Examples of emulsifiers which can be used are: calcium alkylarylsulfonates such as Ca dodecylbenzenesulfonate or non-ionic emulsifiers such as fatty acid polyglycol esters, alkyl-aryl polyglycol ethers, fatty alcohol polyglycol ethers, propylene oxide/ethylene oxide condensation products, fatty alcohol propylene oxide/ethylene oxide condensation products, alkyl polyglycol ethers, sorbitan fatty acid esters, polyoxyethylene sorbitan fatty acid esters or polyoxyethylene sorbitol esters.

Dusting agents can be obtained by milling the active substance with finely divided solid substances, for example talc, natural clays such as kaolin, bentonite, pyrophillite or diatomaceous earth.

Granules can be prepared either by spraying the active substance onto adsorbent granulated inert material or by applying active substance concentrate by means of binders, for example polyvinyl alcohol, sodium polyacrylate or else mineral oils, to the surface of carriers such as sand, kaolinite or of granulated inert material. It is also possible for suitable active substances to be granulated in the manner customary for the preparation of fertilizer granules, if desired mixed with fertilizers.

The agents according to the invention contain the active substances of the formula (I) in an amount of from 2 to 90% by weight as a rule.

The active substance concentration in wettable powders is, for example, about 10 to 90% by weight, the remainder up to 100% by weight comprises customary formulating constituents. In the case of emulsifiable concentrates, the active substance concentration can be about 5 to 80% by weight. Formulations in the form of dusts usually contain 5 to 20% by weight of active substance, and sprayable solutions contain about 2 to 20% by weight. In the case of granules the content of active substance depends partly on whether the active compound is in liquid or solid form and which granulating auxiliaries, fillers etc. are used.

In addition, the said active substance formulations contain, where appropriate, the adhesives, wetting agents, dispersing agents, emulsifiers, penetrating agents or solvents or fillers or carriers customary in each case.

Formulations of these types mentioned above are described in, for example: Winnacker-Küchler, "Chemische Technologie" (Chemical Technology), volume 7, published by C. Hauser, Munich, 4th edition, 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The formulating auxiliaries to be used for these formulations (inert materials, emulsifiers, wetting agents, surfactants, solvents etc.) are described, for example in Marschen, "Solvents Guide", 2nd Ed., Interscience, N.Y. 1950; McCutcheon's, "Detergents and Emulsifiers Annual", MC Publ. Corp., Ridgewood, N.J.; Sisley and Wood or "Encyclopedia of Surface Active Agents", Chem. Publ. Co. Inc., N.Y. 1964.

For use, the concentrates which are in the conventional commercial form are, where appropriate, diluted in a customary manner, for example in the case of wettable powders, emulsifiable concentrates, dispersions and, in some cases also microgranules, using water. Formulations in the form of dusts and granules, as well as sprayable solutions, are not normally diluted with further inert substances before use.

The amount which needs to be used varies with the outside conditions such as temperature, moisture etc. It can vary within wide limits, for example between 0.005 and 10.0 kg/ha or more active substance, but it is preferably between 0.01 and 5 kg/ha.

Also possible are, where appropriate, mixtures or mixed formulations with other active substances such as, for example, insecticides, acaricides, herbicides, fertilizers, growth regulators or fungicides.

The invention is explained in detail by the Examples which follow.

FORMULATION EXAMPLES

A. A dusting agent is obtained by mixing 10 parts by weight of active substance and 90 parts by weight of talc or inert substance and comminuting in a cross beater mill.

B. A wettable powder which is readily dispersible in water is obtained by mixing 25 parts by weight of active substance, 64 parts by weight of kaolin containing silica as inert substance, 10 parts by weight of potassium ligninsulfonate and 1 part by weight of sodium oleoylmethyltaurate as wetting and dispersing agents and milling in a pinned disk mill.

C. A dispersion concentrate which is readily dispersible in water is obtained by mixing 20 parts by weight of active substance with 6 parts by weight of alkylphenol polyglycol ether (®Triton X 207), 3 parts by weight of isotridecanol polyglycol ether with, on average, 8 ethylene oxide units (EO) and 71 parts by weight of paraffin mineral oil (boiling range, for example, about 255° to above 377° C.) and milling in a ball mill to a fineness of below 5 microns.

D. An emulsifiable concentrate is obtained from 15 parts by weight of active substance, 75 parts by weight of cyclohexanone as solvent and 10 parts by weight of ethoxylated nonylphenol (10 EO) as emulsifier.

CHEMICAL EXAMPLES

N-(β-Ethylsulfonylethyl)-n-butylamine

A solution of 15.7 g of chloroethyl ethyl sulfone in 50 ml of toluene is added dropwise within 10 min to a solution of 73 g of n-butylamine and 10.1 g of triethylamine in 100 ml of toluene at an internal temperature of 50° C. The mixture is stirred at 50° C. for 5 h and allowed to cool to room temperature, the precipitate is filtered off with suction, and the filtrate is concentrated in a rotary evaporator. The remaining yellow oil (18.7 g) is reacted without further purification.

Ethyl β-methylaminoethyl sulfone

Gaseous methylamine is passed to saturation (about 30 min) into a solution of 15.7 g of chloroethyl ethyl sulfone in 100 ml of toluene at an internal temperature of 50° C. The mixture is stirred at 50° C. for 3 h, the precipitate is filtered off with suction, and the filtrate is concentrated in a rotary evaporator. The remaining yellow mobile liquid (12.3 g) is reacted without further purification.

N-[N-(β-Ethylsulfonylethyl)-N-methyl]sulfamoyl-N'-(4,6-dimethoxypyrimid-2-yl)-urea (Example No. 235)

A solution of 7.1 g of chlorosulfonyl isocyanate in 50 ml of methylene chloride is added dropwise at −78° C. to a solution of 7.8 g of 2-amino-4,6-dimethoxypyrimidine in 50 ml of CH$_2$Cl$_2$. The mixture is allowed to warm to −30° C., and a solution of 7.6 g of ethyl β-methylaminoethyl sulfone and 5.1 g of triethylamine in 50 ml of methylene chloride is added dropwise. The mixture is allowed to warm to room temperature and is stirred for 16 hours. The reaction mixture is washed with 100 ml each of 2-normal hydrochloric acid and water, dried over magnesium sulfate and concentrated. Trituration of the residue with ether yields 10.5 g of product.

Melting point = 150°–151° C.

Methylmercaptomethylmethylammonium chloride 20 g of triazine in 350 ml of acetonitrile are cooled to −30° C. and then, at −30° C., 18.6 g gaseous HCl are passed in. The mixture is stirred for 10 min and then 24 g of methyl mercaptan are added. The mixture is slowly warmed to room temperature and left to stand for 24 hours. The reaction mixture is concentrated in a rotary evaporator, and the residue is stirred with methylene chloride and filtered off with suction, resulting in 38.7 g of product.

N-[(4,5-Dimethylpyrimid-2-yl-aminocarbonyl]-N'-(methylmercaptomethyl)-N'-methyl-aminosulfonamide (Example No. 1)

2.4 ml of chlorosulfonyl isocyanate are dissolved in 30 ml of methylene chloride and cooled to −20° C. Then 3.08 g of solid 2-amino-4,6-dimethylpyrimidine are added and the mixture is then stirred for 0.5 hours. It is allowed to warm to room temperature, resulting in a clear solution. It is then again cooled to −70° C., and a mixture of 6.9 ml of triethylamine and 3.19 g of methylmercaptomethylmethylammonium chloride in 30 ml of methylene chloride is added dropwise. The mixture is stirred at −70° C. for 0.5 hours and at room temperature for 1 hour. Then water is added and the mixture is extracted with methylene chloride. The organic phase is stirred several times with acetonitrile. This results in 3.2 g of product. Melting point = 138°–140° C.

N-[(4,6-Dimethyl-pyrimid-2-yl-aminocarbonyl]-N'-(methylsulfonylmethyl)-N'-methyl-aminosulfonamide (Example No. 12)

3.19 g of N-[(4,6-Dimethyl-pyrimid-2-yl-aminocarbonyl]-N'-methylmercaptomethyl-N'-methyl-aminosulfonamide are dissolved in 60 ml of glacial acetic acid. To this are added dropwise, at 0° C., 100 ml of a 3% strength KMnO$_4$ solution. The mixture is stirred at room temperature for 2 hours. It is then diluted with ice-water, and sulfur dioxide is passed in until decolorization has occurred. The resulting solid is filtered off with suction and washed with water. 2.2 g of product are obtained after drying in air. Melting point = 146°–148° C.

The compounds listed in Table 1 are obtained in analogy to the Examples described above.

TABLE 1

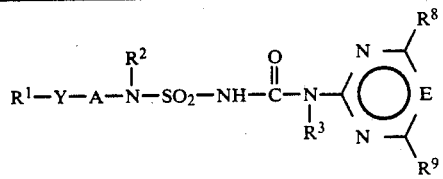

| Ex. No. | A | —Y—R$^1$ | R$^2$ | R$^3$ | R$^8$ | R$^9$ | E | m.p. (°C.) |
|---|---|---|---|---|---|---|---|---|
| 1 | CH$_2$ | —S—CH$_3$ | —CH$_3$ | H | CH$_3$ | CH$_3$ | CH | 138–140 |
| 2 | " | " | " | H | OCH$_3$ | CH$_3$ | " | |
| 3 | " | " | " | H | OCH$_3$ | OCH$_3$ | " | 152–154 |
| 4 | " | " | " | H | " | Cl | " | |
| 5 | " | " | " | H | OCHF$_2$ | CH$_3$ | " | |
| 6 | " | " | " | H | " | CF$_3$ | " | |
| 7 | " | " | " | H | " | OCHF$_2$ | " | |

TABLE 1-continued $$R^1-Y-A-\underset{R^2}{N}-SO_2-NH-\overset{O}{\underset{}{C}}-\underset{R^3}{N}-\underset{}{\overset{N}{\underset{N}{\diagdown}}}\overset{R^8}{\underset{R^9}{\diagup}}E$$

| Ex. No. | A | —Y—R¹ | R² | R³ | R⁸ | R⁹ | E | m.p. (°C.) |
|---|---|---|---|---|---|---|---|---|
| 8 | " | " | " | H | $CH_3$ | Cl | " | |
| 9 | " | " | " | H | $OCH_3$ | Br | " | |
| 10 | " | " | " | H | " | $NHCH_3$ | " | |
| 11 | " | " | " | H | $OCHF_2$ | $OCH_3$ | " | |
| 12 | " | $-SO_2-CH_3$ | " | H | $CH_3$ | $CH_3$ | " | 146–148 |
| 13 | " | " | " | H | $OCH_3$ | $CH_3$ | " | |
| 14 | " | " | " | H | " | $OCH_3$ | " | 176–178 |
| 15 | " | " | " | H | " | Cl | " | |
| 16 | " | " | " | H | $OCHF_2$ | $CH_3$ | " | |
| 17 | " | " | " | H | " | $CF_2$ | " | |
| 18 | " | " | " | H | " | $OCHF_2$ | " | |
| 19 | " | " | " | H | $CH_3$ | Cl | " | |
| 20 | " | " | " | H | $OCH_3$ | Br | " | |
| 21 | $CH_2$ | $-SO_2-CH_3$ | $-CH_3$ | H | $OCH_3$ | $NHCH_3$ | CH | |
| 22 | " | " | " | H | $OCHF_2$ | $OCH_3$ | " | |
| 23 | " | " | " | H | $CH_3$ | $CH_3$ | " | 140–142 DECOMP. |
| 24 | " | " | " | H | $OCH_3$ | $CH_3$ | " | |
| 25 | " | " | " | H | " | $OCH_3$ | " | 135–138 DECOMP. |
| 26 | " | " | " | H | " | Cl | " | |
| 27 | " | " | " | H | $OCHF_2$ | $CH_3$ | " | |
| 28 | " | " | " | H | " | $CF_3$ | " | |
| 29 | " | " | " | H | " | $OCHF_2$ | " | |
| 30 | " | " | " | H | $CH_3$ | Cl | " | |
| 31 | " | " | " | H | $OCH_3$ | Br | " | |
| 32 | " | " | " | H | " | $NHCH_3$ | " | |
| 33 | " | " | " | H | " | $OCH_3$ | " | |
| 34 | " | $-SO_2-C_2H_5$ | " | H | $CH_3$ | $CH_3$ | " | |
| 35 | " | " | " | H | $OCH_3$ | $CH_3$ | " | |
| 36 | " | " | " | H | " | $OCH_3$ | " | |
| 37 | " | " | " | H | " | Cl | " | |
| 38 | " | " | " | H | $OCHF_2$ | $CH_3$ | " | |
| 39 | " | " | " | H | " | $CF_3$ | " | |
| 40 | " | " | " | H | " | $OCHF_2$ | " | |
| 41 | " | " | " | H | $CH_3$ | Cl | " | |
| 42 | " | " | " | H | $OCH_3$ | Br | " | |
| 43 | " | " | " | H | " | $NHCH_3$ | " | |
| 44 | " | " | " | H | $OCHF_2$ | $OCH_3$ | " | |
| 45 | " | $-SO_2-CH_3$ | " | H | $OCH_3$ | $OCH_3$ | N | |
| 46 | $CH_2$ | $-SO_2-CH_3$ | $-CH_3$ | H | $OCHF_2$ | $OCHF_2$ | N | |
| 47 | " | " | " | H | $CH_3$ | $CH_3$ | N | |
| 48 | " | $-SCH_3$ | " | H | $OCH_3$ | $OCH_3$ | N | |
| 49 | " | " | " | H | $CH_3$ | $OCHF_2$ | N | |
| 50 | " | $-S-CH_2-C_6H_5$ | " | H | $CH_3$ | $CH_3$ | CH | 149–152 DECOMP. |
| 51 | " | " | " | H | $OCH_3$ | $CH_3$ | " | |
| 52 | " | " | " | H | $OCH_3$ | $OCH_3$ | " | 114–117 DECOMP. |
| 53 | " | " | " | H | $OCH_3$ | Cl | " | |
| 54 | " | " | " | H | $OCHF_2$ | $CH_3$ | " | |
| 55 | " | " | " | H | $OCHF_2$ | $CF_3$ | " | |
| 56 | " | " | " | H | $OCHF_2$ | $OCHF_2$ | " | |
| 57 | " | " | " | H | $CH_3$ | Cl | " | |
| 58 | " | " | " | H | $OCH_3$ | Br | " | |
| 59 | " | " | " | H | $OCH_3$ | $NHCH_3$ | " | |
| 60 | " | " | " | H | $OCHF_2$ | $OCH_3$ | " | |
| 61 | " | " | $-CH(CH_3)_2$ | H | $CH_3$ | $CH_3$ | " | 136–138 |
| 62 | " | " | " | H | $OCH_3$ | $CH_3$ | " | |
| 63 | " | " | " | H | $OCH_3$ | $OCH_3$ | " | 119–121 |
| 64 | " | " | " | H | $OCH_3$ | Cl | " | |
| 65 | " | " | " | H | $OCHF_2$ | $CH_3$ | " | |
| 66 | " | " | " | H | " | $CF_3$ | " | |
| 67 | " | " | " | H | " | $OCHF_2$ | " | |
| 68 | " | " | " | H | $CH_3$ | Cl | " | |
| 69 | " | " | " | H | $OCH_3$ | Br | " | |
| 70 | " | " | " | H | $OCH_3$ | $NHCH_3$ | " | |
| 71 | " | " | " | H | $OCHF_2$ | $OCH_3$ | " | |
| 72 | $CH_2$ | $-SO_2-CH_3$ | $-CH_3$ | $CH_3$ | $OCH_3$ | $OCH_3$ | N | |
| 73 | " | " | " | " | $CH_3$ | $OCHF_2$ | N | |
| 74 | " | " | " | H | $OCH_3$ | $OCH_3$ | N | |

TABLE 1-continued $$R^1-Y-A-\underset{R^2}{N}-SO_2-NH-\underset{O}{\overset{\|}{C}}-\underset{R^3}{N}-\underset{N}{\overset{N}{\diagup}}\underset{R^9}{\overset{R^8}{\diagdown}}E$$

| Ex. No. | A | —Y—R¹ | R² | R³ | R⁸ | R⁹ | E | m.p. (°C.) |
|---|---|---|---|---|---|---|---|---|
| 75 | " | " | " | CH₃ | OCH₃ | CF₃ | N | |
| 76 | " | —S—CH₃ | " | " | OCH₃ | OCH₃ | CH | |
| 77 | " | " | " | " | OCHF₂ | OCHF₂ | CH | |
| 78 | " | " | " | " | OCH₃ | Br | " | |
| 79 | " | —SO₂—CH₂C₆H₅ | " | H | CH₃ | CH₃ | " | 132–135 DECOMP. |
| 80 | " | " | " | " | OCH₃ | CH₃ | " | |
| 81 | " | " | " | " | OCH₃ | OCH₃ | " | 156–158 DECOMP. |
| 82 | " | " | " | " | OCH₃ | Cl | " | |
| 83 | " | " | " | " | OCHF₂ | CH₃ | " | |
| 84 | " | " | " | " | OCHF₂ | CF₃ | " | |
| 85 | " | " | " | " | OCHF₂ | OCHF₂ | " | |
| 86 | " | " | " | " | CH₃ | Cl | " | |
| 87 | " | " | " | " | OCH₃ | Br | " | |
| 88 | " | " | " | " | OCH₃ | NHCH₃ | " | |
| 89 | " | " | " | " | OCHF₂ | OCH₃ | " | |
| 90 | " | —S—CH₂CO₂CH₃ | " | " | CH₃ | CH₃ | " | 124–126 |
| 91 | " | " | " | " | OCH₃ | CH₃ | " | |
| 92 | " | " | " | " | OCH₃ | OCH₃ | " | 128–131 |
| 93 | " | " | " | " | OCH₃ | Cl | " | |
| 94 | " | " | " | " | OCHF₂ | CH₃ | " | |
| 95 | " | " | " | " | OCHF₂ | CF₃ | " | |
| 96 | " | " | " | " | OCHF₂ | OCHF₂ | " | |
| 97 | " | " | " | " | CH₃ | Cl | " | |
| 98 | CH₂ | —S—CH₂CO₂CH₃ | CH₃ | H | OCH₃ | Br | CH | |
| 99 | " | " | " | " | OCH₃ | NHCH₃ | " | |
| 100 | " | " | " | " | OCHF₂ | OCH₃ | " | |
| 101 | " | " | " | CH₃ | OCH₃ | OCH₃ | " | |
| 102 | " | " | " | " | OCH₃ | OCH₃ | N | |
| 103 | " | " | " | " | OCH₃ | CF₃ | N | |
| 104 | " | " | " | " | OCHF₂ | OCHF₂ | CH | |
| 105 | " | " | " | " | OCH₃ | Br | " | |
| 106 | " | —S—CH₃ | C₂H₅ | H | CH₃ | CH₃ | " | 129–131 |
| 107 | " | " | " | " | OCH₃ | CH₃ | " | |
| 108 | " | " | " | " | OCH₃ | OCH₃ | " | 116–118 |
| 109 | " | " | " | " | OCH₃ | Cl | " | |
| 110 | " | " | " | " | OCHF₂ | CH₃ | " | |
| 111 | " | " | " | " | OCHF₂ | CF₃ | " | |
| 112 | " | " | " | " | OCHF₂ | OCHF₂ | " | |
| 113 | " | " | " | " | CH₃ | Cl | " | |
| 114 | " | " | " | " | OCH₃ | Br | " | |
| 115 | " | " | " | " | OCH₃ | NHCH₃ | " | |
| 116 | " | " | " | " | OCHF₂ | OCH₃ | " | |
| 117 | " | —SCOCH₃ | —CH(CH₃)₂ | " | CH₃ | CH₃ | " | 152–154 DECOMP. |
| 118 | " | " | " | " | OCH₃ | CH₃ | " | |
| 119 | " | " | " | " | OCH₃ | OCH₃ | " | 155–147 DECOMP. |
| 120 | " | " | " | " | OCH₃ | Cl | " | |
| 121 | " | " | " | " | OCHF₂ | CH₃ | " | |
| 122 | " | " | " | " | OCHF₂ | CF₃ | " | |
| 123 | " | " | " | " | " | OCHF₂ | " | |
| 124 | CH₂ | —SCOCH₃ | —CH(CH₃)₂ | H | CH₃ | Cl | CH | |
| 125 | " | " | " | " | OCH₃ | Br | " | |
| 126 | " | " | " | " | OCH₃ | NHCH₃ | " | |
| 127 | " | " | " | " | OCHF₂ | OCH₃ | " | |
| 128 | " | —SCH₃ | —C₂H₅ | CH₃ | OCH₃ | OCH₃ | " | |
| 129 | " | " | " | " | " | Br | " | |
| 130 | " | " | " | H | OCH₃ | OCH₃ | N | |
| 131 | " | " | " | " | OCHF₂ | OCHF₂ | N | |
| 132 | " | " | " | CH₃ | CH₃ | Cl | CH | |
| 133 | " | —SCH₂CH₂CO₂CH₃ | CH₃ | H | CH₃ | CH₃ | " | 134–136 |
| 134 | " | " | " | " | OCH₃ | CH₃ | " | |
| 185 | " | " | " | " | " | OCH₃ | " | 131–133 |
| 136 | " | " | " | " | " | Cl | " | |
| 137 | " | " | " | " | OCHF₂ | CH₃ | " | |
| 138 | " | " | " | " | " | CF₃ | " | |
| 139 | " | " | " | " | " | OCHF₂ | " | |
| 140 | " | " | " | " | CH₃ | Cl | " | |
| 141 | " | " | " | " | OCH₃ | Br | " | |

TABLE 1-continued

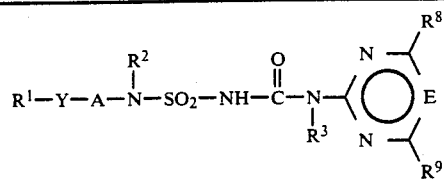

| Ex. No. | A | —Y—R¹ | R² | R³ | R⁸ | R⁹ | E | m.p. (°C.) |
|---|---|---|---|---|---|---|---|---|
| 142 | " | " | " | " | OCH₃ | NHCH₃ | " | |
| 143 | " | " | " | " | OCHF₂ | OCH₃ | " | |
| 144 | " | —S—C₆H₄-2-CO₂C₂H₅ | " | " | CH₃ | CH₃ | " | 145–147 |
| 145 | " | " | " | " | OCH₃ | CH₃ | " | |
| 146 | " | " | " | " | OCH₃ | OCH₃ | " | 118 |
| 147 | " | " | " | " | OCH₃ | Cl | " | |
| 148 | " | " | " | " | OCHF₂ | CH₃ | " | |
| 149 | " | " | " | " | OCHF₂ | CF₃ | " | |
| 150 | CH₂ | —S—C₆H₄-2-CO₂C₂H₅ | CH₃ | H | OCHF₂ | OCHF₂ | CH | |
| 151 | " | " | " | " | CH₃ | Cl | " | |
| 152 | " | " | " | " | OCH₃ | Br | " | |
| 153 | " | " | " | " | OCH₃ | NHCH₃ | " | |
| 154 | " | " | " | " | OCHF₂ | OCH₃ | " | |
| 155 | " | " | " | CH₃ | OCH₃ | OCH₃ | " | |
| 156 | " | " | " | " | CH₃ | CH₃ | " | |
| 157 | " | " | " | H | OCH₃ | OCH₃ | N | |
| 158 | " | " | " | " | CH₃ | CH₃ | N | |
| 159 | " | " | " | " | CH₃ | CH₃ | CH | 138–140 |
| 160 | " | " | " | H | OCH₃ | CH₃ | CH | |
| 161 | " | " | " | H | OCH₃ | OCH₃ | CH | 130 |
| 162 | " | " | " | H | OCH₃ | Cl | CH | |
| 163 | " | " | " | H | OCHF₂ | CH₃ | " | |
| 164 | " | " | " | " | OCHF₂ | CF₃ | " | |
| 165 | " | " | " | " | OCHF₂ | OCHF₂ | " | |
| 166 | " | " | " | " | CH₃ | Cl | " | |
| 167 | " | " | " | " | OCH₃ | Br | " | |
| 168 | " | " | " | " | OCH₃ | NHCH₃ | " | |
| 169 | " | " | " | " | OCHF₂ | OCH₃ | " | |
| 170 | " | —SCH₃ | —CH₂CH₂CH₃ | " | CH₃ | CH₃ | " | 128–131 |
| 171 | " | " | " | " | OCH₃ | CH₃ | " | |
| 172 | " | " | " | " | OCH₃ | OCH₃ | " | 142–144 |
| 173 | " | " | " | " | OCH₃ | Cl | " | |
| 174 | " | " | " | " | OCHF₂ | CH₃ | " | |
| 175 | " | " | " | " | OCHF₂ | CF₃ | " | |
| 176 | CH₂ | —SCH₃ | —CH₂CH₂CH₃ | H | OCHF₂ | OCHF₂ | CH | |
| 177 | " | " | " | " | CH₃ | Cl | " | |
| 178 | " | " | " | " | OCH₃ | Br | " | |
| 179 | " | " | " | " | OCH₃ | NHCH₃ | " | |
| 180 | " | " | " | " | OCHF₂ | OCH₃ | " | |
| 181 | " | " | " | CH₃ | OCH₃ | OCH₃ | " | |
| 182 | " | " | " | " | CH₃ | CH₃ | " | |
| 183 | " | " | " | H | OCH₃ | OCH₃ | N | |
| 184 | " | " | " | " | CH₃ | CH₃ | N | |
| 185 | " | —SC₆H₄-4-Cl | —CH₃ | " | CH₃ | CH₃ | CH | |
| 186 | " | " | " | " | OCH₃ | CH₃ | " | |
| 187 | " | " | " | " | OCH₃ | OCH₃ | " | 151–153 |
| 188 | " | " | " | " | " | Cl | " | |
| 189 | " | " | " | " | OCHF₂ | CH₃ | " | |
| 190 | " | " | " | " | OCHF₂ | CF₃ | " | |
| 191 | " | " | " | " | OCHF₂ | OCHF₂ | " | |
| 192 | " | " | " | " | CH₃ | Cl | " | |
| 193 | " | " | " | " | OCH₃ | Br | " | |
| 194 | " | " | " | " | OCH₃ | NHCH₃ | " | |
| 195 | " | " | " | " | OCHF₂ | OCH₃ | " | |
| 196 | " | " | " | " | CH₃ | CH₃ | " | |
| 197 | " | " | " | " | OCH₃ | CH₃ | " | |
| 198 | " | " | " | " | OCH₃ | OCH₃ | " | |
| 199 | " | " | " | " | OCH₃ | Cl | " | |
| 200 | " | " | " | " | OCHF₂ | CH₃ | " | |
| 201 | " | " | " | " | OCHF₂ | CF₃ | " | |
| 202 | CH₂ | —SCH₂C₆H₄-2-Cl | —CH₃ | H | OCHF₂ | OCHF₂ | CH | |
| 203 | " | " | " | " | CH₃ | Cl | " | |
| 204 | " | " | " | " | OCH₃ | Br | " | |
| 205 | " | " | " | " | OCH₃ | NHCH₃ | " | |
| 206 | " | " | " | " | OCHF₂ | OCH₃ | " | |
| 207 | " | " | " | CH₃ | OCH₃ | OCH₃ | " | |
| 208 | " | " | " | " | CH₃ | CH₃ | " | |
| 209 | " | " | " | H | OCH₃ | OCH₃ | N | |
| 210 | " | " | " | " | CH₃ | CH₃ | N | |
| 211 | CH₂CH₂ | —SO₂C₂H₅ | —CH₂CH₂CH₃ | " | CH₃ | CH₃ | CH | 127–130 |
| 212 | " | " | " | " | OCH₃ | CH₃ | " | |

TABLE 1-continued

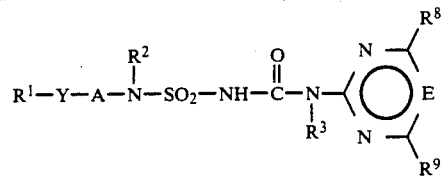

| Ex. No. | A | —Y—R¹ | R² | R³ | R⁸ | R⁹ | E | m.p. (°C.) |
|---|---|---|---|---|---|---|---|---|
| 213 | " | " | " | " | OCH₃ | OCH₃ | " | |
| 214 | " | " | " | " | OCH₃ | Cl | " | |
| 215 | " | " | " | " | OCHF₂ | CH₃ | " | |
| 216 | " | " | " | " | OCHF₂ | CF₃ | " | |
| 217 | " | " | " | " | OCHF₂ | OCHF₂ | " | |
| 218 | " | " | " | " | CH₃ | Cl | " | |
| 219 | " | " | " | " | OCH₃ | Br | " | |
| 220 | " | " | " | " | OCH₃ | NHCH₃ | " | |
| 221 | " | " | " | " | OCHF₂ | OCH₃ | " | |
| 222 | " | " | —CH(CH₃)₂ | " | CH₃ | CH₃ | " | 108–111 |
| 223 | " | " | " | " | OCH₃ | CH₃ | " | |
| 224 | " | " | " | " | OCH₃ | OCH₃ | " | |
| 225 | " | " | " | " | OCH₃ | Cl | " | |
| 226 | " | " | " | " | OCHF₂ | CH₃ | " | |
| 227 | CH₂CH₂ | —SO₂C₂H₅ | —CH(CH₃)₂ | H | OCHF₂ | CF₃ | CH | |
| 228 | " | " | " | " | OCHF₂ | OCHF₂ | " | |
| 229 | " | " | " | " | CH₃ | Cl | " | |
| 230 | " | " | " | " | OCH₃ | Br | " | |
| 231 | " | " | " | " | OCH₃ | NHCH₃ | " | |
| 232 | " | " | " | " | OCHF₂ | OCH₃ | " | |
| 233 | " | " | —CH₃ | " | CH₃ | CH₃ | " | 144–146 |
| 234 | " | " | " | " | OCH₃ | CH₃ | " | |
| 235 | " | " | " | " | OCH₃ | OCH₃ | " | 150–151 |
| 236 | " | " | " | " | OCH₃ | Cl | " | |
| 237 | " | " | " | " | OCHF₂ | CH₃ | " | |
| 238 | " | " | " | " | " | CF₃ | " | |
| 239 | " | " | " | " | " | OCHF₂ | " | |
| 240 | " | " | " | " | CH₃ | Cl | " | |
| 241 | " | " | " | " | OCH₃ | Br | " | |
| 242 | " | " | " | " | OCH₃ | NHCH₃ | " | |
| 243 | " | " | " | " | OCHF₂ | OCH₃ | " | |
| 244 | " | " | —(CH₂)₃CH₃ | " | CH₃ | CH₃ | " | 106–109 |
| 245 | " | " | " | " | OCH₃ | CH₃ | " | |
| 246 | " | " | " | " | OCH₃ | OCH₃ | " | |
| 247 | " | " | " | " | OCH₃ | Cl | " | |
| 248 | " | " | " | " | OCHF₂ | CH₃ | " | |
| 249 | " | " | " | " | OCHF₂ | CF₃ | " | |
| 250 | " | " | " | " | OCHF₂ | OCHF₂ | " | |
| 251 | " | " | " | " | CH₃ | Cl | " | |
| 252 | " | " | " | " | OCH₃ | Br | " | |
| 253 | CH₂CH₂ | —SO₂C₂H₅ | —(CH₂)₃CH₃ | H | OCH₃ | NHCH₃ | CH | |
| 254 | " | " | " | " | OCHF₂ | OCH₃ | " | |
| 255 | " | —SO₂C₆H₅ | —CH₂CO₂C₂H₅ | " | CH₃ | CH₃ | " | Oil |
| 256 | " | " | " | " | OCH₃ | CH₃ | " | |
| 257 | " | " | " | " | OCH₃ | OCH₃ | " | |
| 258 | " | " | " | " | OCH₃ | Cl | " | |
| 259 | " | " | " | " | OCHF₂ | CH₃ | " | |
| 260 | " | " | " | " | OCHF₂ | CF₃ | " | |
| 261 | " | " | " | " | " | OCHF₂ | " | |
| 262 | " | " | " | " | CH₃ | Cl | " | |
| 263 | " | " | " | " | OCH₃ | Br | " | |
| 264 | " | " | " | " | " | NHCH₃ | " | |
| 265 | " | " | " | " | OCHF₂ | OCH₃ | " | |
| 266 | " | —SO₂C₂H₅ | —C₆H₁₁ | " | CH₃ | CH₃ | " | 156–158 |
| 267 | " | " | " | " | OCH₃ | CH₃ | " | |
| 268 | " | " | " | " | OCH₃ | OCH₃ | " | |
| 269 | " | " | " | " | OCH₃ | Cl | " | |
| 270 | " | " | " | " | OCHF₂ | CH₃ | " | |
| 271 | " | " | " | " | OCHF₂ | CF₃ | " | |
| 272 | " | " | " | " | OCHF₂ | OCHF₂ | " | |
| 273 | " | " | " | " | CH₃ | Cl | " | |
| 274 | " | " | " | " | OCH₃ | Br | " | |
| 275 | " | " | " | " | OCH₃ | NHCH₃ | " | |
| 276 | " | " | " | " | OCHF₂ | OCH₃ | " | |
| 277 | CH₂CH₂ | —SO₂CH₃ | —CH₃ | H | CH₃ | CH₃ | CH | |
| 278 | " | " | " | " | OCH₃ | CH₃ | " | |
| 279 | " | " | " | " | " | OCH₃ | " | |
| 280 | " | " | " | " | " | Cl | " | |
| 281 | " | " | " | " | OCHF₂ | CH₃ | " | |
| 282 | " | " | " | " | OCHF₂ | CF₃ | " | |
| 283 | " | " | " | " | OCHF₂ | OCHF₂ | " | |

TABLE 1-continued

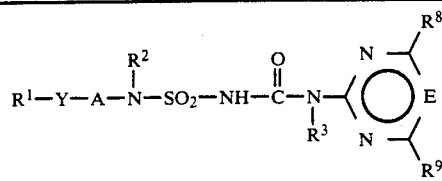

| Ex. No. | A | —Y—R¹ | R² | R³ | R⁸ | R⁹ | E | m.p. (°C.) |
|---|---|---|---|---|---|---|---|---|
| 284 | " | " | " | " | CH₃ | Cl | " | |
| 285 | " | " | " | " | OCH₃ | Br | " | |
| 286 | " | " | " | " | OCH₃ | NHCH₃ | " | |
| 287 | " | " | " | " | OCHF₂ | OCH₃ | " | |
| 288 | " | " | —CH₂CH₃ | " | CH₃ | CH₃ | " | |
| 289 | " | " | " | " | OCH₃ | CH₃ | " | |
| 290 | " | " | " | " | " | OCH₃ | " | |
| 291 | " | " | " | " | " | Cl | " | |
| 292 | " | " | " | " | OCHF₂ | CH₃ | " | |
| 293 | " | " | " | " | " | CF₃ | " | |
| 294 | " | " | " | " | " | OCHF₂ | " | |
| 295 | " | " | " | " | CH₃ | Cl | " | |
| 296 | " | " | " | " | OCH₃ | Br | " | |
| 297 | " | " | " | " | OCH₃ | NHCH₃ | " | |
| 298 | " | " | " | " | OCHF₂ | OCH₃ | " | |
| 299 | CH₂ | —SCH₃ | —CH₃ | H | OC₂H₅ | OC₂H₅ | " | 128 |
| 300 | " | —SO₂CH₃ | " | " | " | " | " | |
| 301 | " | —SC₂H₅ | " | " | " | " | " | 119 |
| 302 | CH₂ | —SO₂C₂H₅ | —CH₃ | H | OC₂H₅ | OC₂H₅ | CH | |
| 303 | " | —SCH₂C₆H₅ | " | " | " | " | " | |
| 304 | " | —SO₂CH₂C₆H₅ | " | " | " | " | " | |
| 305 | " | —SCH₂CO₂CH₃ | " | " | " | " | " | |
| 306 | " | —SCOCH₃ | " | " | " | " | " | |
| 307 | " | —SCH₂CH₂CO₂CH₃ | " | " | " | " | " | |
| 308 | " | —SC₆H₄-2-CO₂C₂H₅ | " | " | " | " | " | |
| 309 | " | —SC₆H₄-2-Cl | " | " | " | " | " | |
| 310 | " | —SCH₂C₆H₄-2-Cl | " | " | " | " | " | |
| 311 | " | " | —C₂H₅ | " | " | " | " | |
| 312 | " | —SC₆H₄-2-Cl | " | " | " | " | " | |
| 313 | " | —SC₆H₄-2-CO₂CH₃ | " | " | " | " | " | |
| 314 | " | —SCH₂CH₂CO₂CH₃ | " | " | " | " | " | |
| 315 | " | —SCH₂CO₂CH₃ | " | " | " | " | " | |
| 316 | " | —SO₂CH₂C₆H₅ | " | " | " | " | " | |
| 317 | " | —SCH₂C₆H₅ | " | " | " | " | " | |
| 318 | " | —SO₂C₂H₅ | " | " | " | " | " | |
| 319 | " | —SC₂H₅ | " | " | " | " | " | |
| 320 | " | —SO₂CH₃ | " | " | " | " | " | |
| 321 | " | —SCH₃ | " | " | " | " | " | |

BIOLOGICAL EXAMPLES

The damage to weed plants and the tolerability by crop plants were scored using a system in which the activity is expressed by figures from 0 to 5. In this:
0 means no effect
1 means 0 to 20% effect or damage
2 means 20 to 40% effect or damage
3 means 40 to 60% effect or damage
4 means 60 to 80% effect or damage
5 means 80 to 100% effect or damage

1. Preemergence on effect weeds

Seeds or pieces of rhizomes of mono- and dicotyledonous weed plants were distributed in sandy loamy soil in plastic pots and covered with soil. The compounds according to the invention which were formulated in the form of wettable powders or emulsion concentrates were then applied as aqueous suspensions or emulsions in various dosages to the surface of the covering soil using an amount of water equivalent to 600 to 800 ha.

After the treatment, the pots were placed in a glass house and kept under good conditions for the growth of the weeds. The visual scoring of the damage to the plants or shoots was carried out after the trial plants had emerged after a trial period of 3 to 4 weeks by comparison with untreated controls. As shown by the scores in Table I, the compounds according to the invention display a good preemergence herbicidal activity against a wide spectrum of graminaceous and other weeds.

2. Postemergence effect on weeds

Seeds or pieces of rhizomes of mono- and dicotyledonous weeds were distributed in sandy loamy soil in plastic pots, covered with soil and raised in a glass house under good conditions for growth. Three weeks after sowing the trial plants were treated at the three-leaf stage.

The compounds according to the invention formulated as wettable powders or as emulsion concentrates were sprayed in various dosages onto the green parts of the plants, using an amount of water equivalent to 600 to 800 ha, and, after the trial plants had stood in the glass house under optimal conditions for growth for about 3 to 4 weeks, the effect of the products was scored visually by comparison with untreated controls.

The agents according to the invention also display a good postemergence herbicidal activity against a wide spectrum of economically important graminaceous and other weeds (Table II).

3. Tolerability by crop plants

In further trials in a glass house, seeds of a large number of crop plants and weeds were distributed in sandy loamy soil and covered with soil.

Some of the pots were immediately treated as described under 1., and the others were placed in the glass house until the plants had developed two or three true leaves and were then sprayed with the substances according to the invention in various dosages as described under 2.

After the application and standing in the glass house for four to five weeks, it was established by visual scoring that the compounds according to the invention left dicotyledonous crops such as, for example, soybean, cotton, rape, sugar beet and potatoes undamaged even at high dosages of active substance in the pre- and post-emergence processes. Some substances additionally spared graminaceous crops such as, for example, barley, wheat, rye, sorghum-millet, corn or rice. Thus, the compounds of the formula I display high selectivity when used to control undesired plant growth in agricultural crops.

TABLE I

Preemergence effect of the compounds according to the invention

| Example No. | Dose (kg a.i./ha) | Herbicidal effect | | | |
|---|---|---|---|---|---|
| | | STM | CRS | SIA | LOM |
| 92 | 0.6 | 2 | 4 | 4 | 2 |
| 106 | 0.6 | 3 | 4 | 5 | 2 |
| 81 | 0.6 | 3 | 5 | 4 | 4 |
| 117 | 0.6 | 2 | 5 | 2 | 2 |
| 25 | 0.6 | 3 | 5 | 3 | 3 |
| 172 | 0.6 | 5 | 3 | 5 | 3 |
| 170 | 0.6 | 5 | 5 | 5 | 5 |
| 3 | 0.6 | 5 | 5 | 5 | 5 |
| 14 | 0.6 | 3 | 5 | 4 | 4 |
| 235 | 0.6 | 5 | 5 | 5 | 4 |
| 211 | 0.6 | 5 | 5 | 5 | 3 |
| 244 | 0.6 | 2 | 3 | 5 | 2 |
| 222 | 0.6 | 1 | 4 | 4 | 2 |
| 233 | 0.6 | 5 | 5 | 5 | 3 |
| 266 | 0.6 | 2 | 5 | 5 | 4 |

STM = *Stellaria media*
CRS = *Chrysanthemum segetum*
SIA = *Sinapis alba*
LOM = *Lolium multiflorum*

TABLE II

Postemergence effect of the compounds according to the invention

| Example No. | Dose (kg a.i./ha) | Herbicidal effect | | | |
|---|---|---|---|---|---|
| | | STM | CRS | SIA | LOM |
| 92 | 0.6 | 2 | 3 | 5 | 1 |
| 1 | 0.6 | 3 | 3 | 4 | 2 |
| 106 | 0.6 | 4 | 4 | 5 | 1 |
| 108 | 0.6 | 3 | 2 | 4 | 2 |
| 81 | 0.6 | 4 | 4 | 4 | 2 |
| 119 | 0.6 | 5 | 2 | 2 | 1 |
| 25 | 0.6 | 4 | 2 | 4 | 2 |
| 172 | 0.6 | 3 | 3 | 3 | 2 |
| 170 | 0.6 | 5 | 5 | 4 | 4 |
| 3 | 0.6 | 5 | 4 | 4 | 3 |
| 14 | 0.6 | 5 | 5 | 5 | 2 |
| 235 | 0.6 | 4 | 5 | 5 | 4 |
| 211 | 0.6 | 5 | 4 | 4 | 3 |

Inhibition of cereal growth

In trials in pans in a glass house, young cereals plants (wheat, barley, rye) in the 3-leaf stage were sprayed until dripping wet with compounds according to the invention in various concentrations of active substance (kg/ha).

After the untreated control plants had grown to a height of about 55 cm, the increment was measured for all the plants, and the inhibition of growth was calculated as a of the increment for the control plants. In addition, the phytotoxic effect of the compounds was observed, with 100% meaning cessation of growth and 0% meaning growth corresponding to that of untreated control plants. It emerged that the compounds have very good growth-regulating properties.

We claim:

1. A compound of the formula (I) or a salt thereof

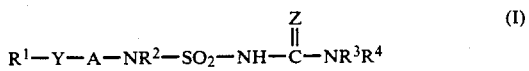

where
  A is a saturated or unsaturated, unbranched or branched $C_1$-$C_{10}$-hydrocarbon radical,
  $R^1$ is $C_1$-$C_8$-alkyl, $C_2$-$C_8$-alkenyl, $C_2$-$C_8$-alkynyl, $C_3$-$C_8$-cycloalkyl, $C_5$-$C_8$-cycloalkenyl or one of the preceding five radicals which is substituted one or more times by halogen or by the radicals selected from the group consisting of $C_1$-$C_6$-alkoxy, $C_2$-$C_6$-alkenyl-oxy, $C_2$-$C_6$-alkynyloxy, $C_1$-$C_6$-alkylthio, $C_1$-$C_6$-alkylsulfinyl, $C_1$-$C_6$-alkyulsulfonyl, $C_3$-$C_6$-cycloalkyl, a radical of a three- to six-membered saturated heterocycle having one oxygen atom in the ring, furyl, phenyl and a phenyl radical which is substituted one or more times by radicals selected from the group consisting of halogen, $C_1$-$C_4$-alkyl, $C_1$-$C_4$-alkoxy, $CF_3$, ($C_1$-$C_4$-alkoxy)-carbonyl and nitro, or
  $R^1$ is phenyl or a phenyl radical which is substituted one or more times by radicals selected from the group consisting of halogen, $C_1$-$C_4$-alkyl, $C_1$-$C_4$-alkoxy, $CF_3$, ($C_1$-$C_4$-alkoxy)-carbonyl and nitro, or
  $R^1$ is a radical of the formula

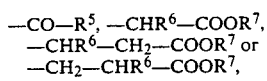

where, in the formulae, $R^5$ is $C_1$-$C_6$-alkyl, $R^6$ is hydrogen, $C_1$-$C_4$-alkyl, phenyl or benzyl and $R^7$ is $C_1$-$C_4$-alkyl, phenyl or benzyl,
  Y is S or $SO_2$,
  $R^2$ is H, $C_1$-$C_8$-alkyl, $C_2$-$C_8$-alkenyl, $C_2$-$C_8$-alkynyl or one of the preceding three radicals which is substituted one or more times by halogen or by radicals selected from the group consisting of $C_1$-$C_6$-alkoxy, $C_2$-$C_6$-alkenyloxy, $C_2$-$C_6$-alkynyloxy, $C_1$-$C_6$-alkylthio, $C_1$-$C_6$-alkylsulfinyl, $C_1$-$C_6$-alkylsulfonyl, ($C_1$-$C_6$-alkoxy)-carbonyl, phenoxycarbonyl, benzyloxycarbonyl and phenyl, or
  $R^2$ is $C_3$-$C_8$-cycloalkyl which is unsubstituted or substituted one or more times by halogen or once or twice by $C_1$-$C_4$-alkoxy or $C_1$-$C_4$-alkylthio, or
  $R^2$ is $C_5$-$C_8$-cycloalkenyl, cyclopropylmethyl, epoxypropyl, furfuryl, tetrahydrofurfuryl, phenoxy-$C_1$-$C_6$-alkyl, phenyl or one of the last two preceding radicals which is substituted in the phenyl ring by halogen, $C_1$-$C_4$-alkyl, $C_1$-$C_4$-alkoxy or nitro, R³ is H, C₁-C₈-alkyl, C₂-C₈-alkenyl, C₂-C₈-alkylnyl or C₁C₄-alkoxy, R⁴ is a radical of the formula

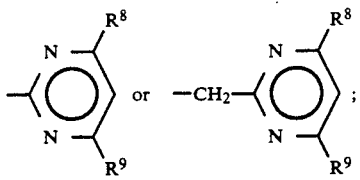

R⁸ and R⁹ are, independently of one another, H, halogen, C₁-C₆-alkyl, C₁-C₆-alkoxy, C₁-C₆-alkylthio or one of the last three preceding radicals which is substituted one or more times by halogen or once or twice by C₁-C₄-alkoxy or C₁-C₄-alkylthio, or R⁸ and R⁹ are, independently of another radical NR¹⁴R¹⁵, C₁-C₆-cycloalkyl, —OCHR¹⁶COOR⁷, C₃-C₅-alkenyl, C₂-C₄-alkynyl, C₃-C₅-alkenyloxy or C₃-C₅-alkynyloxy, R¹⁴ and R¹⁵ denote, independently of one another, H, C₁-C₄-alkyl, C₂-C₄-alkenyl or C₃-C₄-alkynyl, R¹⁶ denotes hydrogen or C₁-C₄-alkyl, R¹⁷ denotes hydrogen or C₁-C₄-alkyl, and Z denotes O or S.

2. A compound as claimed in claim 1, wherein
A is a radical of the formula —CH₂— or —CH₂—CH₂—, R¹ is C₁-C₄-alkyl, a C₁-C₄-alkyl radical which is substituted one or more times by halogen or once or twice by C₁-C₄-alkoxy, or R¹ is C₃-C₈-cycloalkyl which is substituted one or more times by halogen or is unsubstituted, or R¹ is benzyl, phenyl or a benzyl or phenyl radical which is substituted in the phenyl ring one or more times by halogen, C₁-C₄-alkyl, C₁-C₄-alkoxy, CF₃, (C₁-C₄-alkoxy)-carbonyl or nitro, or R¹ is a radical of the formula

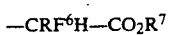
—CRF⁶H—CO₂R⁷ in which R⁶ and R⁷ are identical or different and each is H, C₁-C₄-alkyl, phenyl or benzyl, R² is C₁-C₄-alkyl which is unsubstituted or substituted one or more times by halogen or by (C₁-C₄-alkoxy)-carbonyl, phenyloxycarbonyl, benzyloxycarbonyl or phenyl, R³ is H, C₁-C₄-alkyl or allyl, R⁴ is a radical of the formula

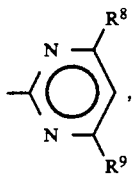

R⁸ and R⁹ are, independently of one another, halogen, C₁-C₄-alkyl, C₁-C₄-alkoxy or one of the last two preceding radicals which is halogenated, and Z denotes O or S.

3. A compound as claimed in claim 1, wherein A is CH₂ or CH₂CH₂,

R¹ is C₁-C₄-alkyl, phenyl, halogenophenyl, benzyl, halogenobenzyl, (C₁-C₄-alkoxy)carbonyl-(C₁-C₄-alkyl) or (C₁-C₄-alkoxy)carbonyl, R² is C₁-C₄-alkyl, C₃-C₅-cycloalkyl or (C₁-C₄-alkoxy)carbonyl-C₁-C₄-alkyl), R³ is hydrogen, R⁸ is C₁-C₄-alkyl or C₁-C₄-alkoxy, R⁹ is C₁-C₄-alkyl or C₁-C₄-alkoxy, and Z is an oxygen atom.

4. A compound as claimed in claim 3, wherein R⁸ is methyl or methoxy and R⁹ is methyl or methoxy.

5. A compound as claimed in claim 1, wherein
R¹ denotes C₁-C₄-alkyl, a C₁-C₄-alkyl radical which is substituted one or more times by halogen or once or twice by C₁-C₄-alkoxy, C₂-C₃-alkenyloxy, C₂-C₃-alkynyloxy, C₁-C₄-alkylthio, C₁-C₄-alkylsulfinyl, C₁-C₄-alkylsulfonyl, phenyl or a phenyl radical which is substituted one to three times by radicals from the group comprising halogen, C₁-C₄-alkyl, C₁-C₄-alkoxy, CF₃, (C₁-C₄-alkoxy)-carbonyl and nitro, or denotes C₃-C₈-cycloalkyl or a C₃-C₈-cycloalkyl radical which is substituted one or more times by halogen or once or twice by C₁-C₄-alkoxy or C₁-C₄-alkylthio, or denotes C₅-C₈-cycloalkenyl, cyclopropylmethyl, epoxydenotes propyl, furfuryl, tetrahydrofurfuryl, benzyl, phenyl or a benzyl or phenyl radical which is substituted in the phenyl ring by one or more radicals from the group comprising halogen, C₁-C₄-alkyl, C₁-C₄-alkoxy, CF₃, (C₁-C₄-alkoxy)-carbonyl and nitro, or denotes a radical of the formula

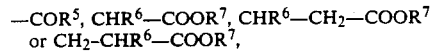
—COR⁵, CHR⁶—COOR⁷, CHR⁶—CH₂—COOR⁷ or CH₂-CHR⁶—COOR⁷,

R⁵ denotes C₁-C₄-alkyl,

R⁶ denotes H, C₁-C₄-alkyl, benzyl or phenyl and

R⁷ denotes H, C₁-C₄-alkyl, benzyl or phenyl.

6. A compound as claimed in claim 1, wherein
R² denotes C₁-C₄-alkyl, a C₁-C₄-alkyl radical which is substituted one or more times by halogen or once or twice by C₁-C₄-alkoxy, C₂-C₄-alkenyloxy, propargyloxy, C₁-C₄-alkylthio, C₁-C₄-alkylsulfinyl, C₁-C₄-alkylsulfonyl, (C₁-C₄-alkoxy)-carbonyl, phenoxycarbonyl, benzyloxycarbonyl or phenyl, or denotes C₃-C₈-cycloalkyl.

7. A compound as claimed in claim 1, wherein
R⁴ denotes a radical of the formula

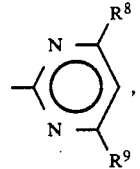

and

R⁸ and R⁹ denote, independently of one another, halogen, C₁-C₄-alkyl, C₁-C₄-alkoxy, C₁-C₄-alkylthio or one of the last three preceding radicals which are substituted one or more times by halogen or once or twice by C₁-C₄-alkoxy, C₁-C₄-alkylthio, or denote a radical NR¹⁴R¹⁵, C₃-C₆-cycloalkyl, —OCHR¹⁶COOR¹⁷, allyl, propargyl, allyloxy or propargyloxy, R¹⁴ and R¹⁵ denote, independently of one another, H or C₁-C₄-alkyl, R¹⁶ denotes H or C₁-C₄-alkyl, and R¹⁷ denotes C₁-C₄-alkyl.

8. A compound as claimed in claim 1, wherein

A denotes a radical of the formula CH₂, CH₂CH₂, CHR, CRR', CH₂CHR or CH₂CRR', where R and R' denote, independently of one another, C₁-C₄-alkyl or C₂-C₄-alkenyl.

9. A compound as claimed in claim 1, wherein

A denotes a radical of the formula —CH₂— or —CH₂—CH₂—,

R¹ denotes C₁-C₄-alkyl, a C₁-C₄-alkyl radical which is substituted one or more times by halogen or once or twice by C₁-C₄-alkoxy, denotes C₃-C₈-cycloalkyl which is substituted one or more times by halogen or is unsubstituted, denotes benzyl, phenyl or a benzyl or phenyl radical which is substituted in the phenyl ring one or more times by halogen, C₁-C₄-alkylo, C₁-C₄-alkoxy, CF₃, (C₁-C₄-alkoxy)-carbonyl or nitro, or denotes a radical of the formula

—CR⁶H—CO₂R⁷ in which R⁶ and R⁷ are identical or different and each denotes H, C₁-C₄-alkyl, phenyl or benzyl, R² denotes C₁-C₄-alkyl which is unsubstituted or substituted one or more times by halogen or by (C₁-C₄-alkoxy)-carbonyl, phenyloxycarbonyl, benzyloxycarbonyl or phenyl, R³ denotes H, C₁-C₄-alkyl or allyl, R⁴ denotes a radical of the formula

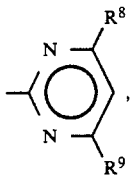

R⁸ and R⁹ denote, independently of one another, halogen, C₁-C₄-alkyl, C₁-C₄-alkoxy or one of the last two preceding radicals which is halogenated, Z denotes O or S.

10. A herbicidal composition which contains an effective amount of a compound of the formula (I), or one of its salts, as claimed in claim 13 in addition to inert carriers.

11. A composition as claimed in claim 10, which contains 2 to 90% by weight of compound of the formula (I) or one of its salts.

12. A plant-growth regulating composition which contains an effective amount of a compound of the formula (I), or one of its salts as claimed in claim 1 in addition to inert carriers.

13. A method for controlling undesired plant growth, which comprises applying a compound of the formula (I), or one of its salts, as claimed in claim 1 in an effective amount between 0.005 and 10.0 kg/ha active substance to the plants or the cultivated area.

14. A method for regulating the growth of plants, which comprises applying an effective amount of a compound of the formula (I), or one of its salts, as claimed in claim 1 to the plants or the cultivated area.

* * * * *

UNITED STATES PATENT AND TRADEMARK OFFICE
CERTIFICATE OF CORRECTION

PATENT NO. : 5,030,270
DATED : July 9, 1991
INVENTOR(S) : Loher et al.

It is certified that error appears in the above-identified patent and that said Letters Patent is hereby corrected as shown below:

At column 22, line 29, change "$C_1$-$C_6$-alkyulsulfo" to --$C_1$-$C_6$-alkylsulfo--; and At column 23, line 19, change "-$OCHR^{16}COOR^7$" to -- -$OCHR^{16}COOR^{17}$ --.

At column 23, line 19, change "$C_1$-$C_6$" to -- $C_3$-$C_6$ --.

Signed and Sealed this

Thirtieth Day of June, 1992

Attest:

DOUGLAS B. COMER

Attesting Officer

Acting Commissioner of Patents and Trademarks